(12) United States Patent
Jenn-Feng et al.

(10) Patent No.: US 6,621,686 B1
(45) Date of Patent: Sep. 16, 2003

(54) IMPLANTABLE MEDICAL DEVICE HAVING FLAT ELECTROLYTIC CAPACITOR FORMED WITH PARTIALLY THROUGH-ETCHED AND THROUGH-HOLE PUNCTURED ANODE SHEETS

(75) Inventors: Yan Jenn-Feng, Maple Grove, MN (US); Darrel F. Untereker, Oak Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 184 days.

(21) Appl. No.: 09/607,830

(22) Filed: Jun. 30, 2000

(51) Int. Cl.$^7$ .............................................. H01G 9/042
(52) U.S. Cl. ....................................... 361/508; 361/503
(58) Field of Search ................................ 361/503–522

(56) References Cited

U.S. PATENT DOCUMENTS

| | | | | |
|---|---|---|---|---|
| 2,444,914 A | * | 7/1948 | Brennan | 175/315 |
| 4,254,775 A | | 3/1981 | Langer | 128/419 |
| 4,548,209 A | | 10/1985 | Wielders et al. | 128/419 D |
| 4,617,611 A | | 10/1986 | Miura et al. | 361/433 |
| 4,663,824 A | | 5/1987 | Kenmochi | 29/570 |

(List continued on next page.)

FOREIGN PATENT DOCUMENTS

WO  WO 00/19470  4/2000 .......... H01G/9/055

OTHER PUBLICATIONS

P. Lunsmann et al., "High Energy Density Capacitors for Implantable Defibrillators," *CARTS 96: 16$^{th}$ Capacitor and Resistor Technology Symposium*, Mar. 11–15, 1996, pp 277–280.

Troup, "Implantable Cardioverters and Defibrillators," *Current Problems in Cardiology*, vol. XIV, No. 12, Dec. 1989, Year Book Medical Publishers, Chicago.

P. Lunsmann et al., "High Energy Density Capacitors for Implantable Defibrillators," *CARTS–Europe 96: 10$^{th}$ European Passive Components Symposium.*, Oct. 7–11, 1996, pp. 35–39.

*Primary Examiner*—Dean A. Reichard
*Assistant Examiner*—Eric Thomas
(74) *Attorney, Agent, or Firm*—Girma Wolde-Michael; Paul H. McDowall

(57) ABSTRACT

Implantable medical devices (IMDs) and their various components, including flat electrolytic capacitors for same, and methods of making and using same, particularly an improved electrolytic capacitor with optimized ESR and anode layer surface area. An electrode stack assembly and electrolyte are located within the interior case chamber of a hermetically sealed capacitor case. The electrode stack assembly comprises a plurality of capacitor layers stacked in registration upon one another, each capacitor layer comprising a cathode layer having a cathode tab, an anode subassembly comprising at least one anode layer having an anode tab, and a separator layer located between adjacent anode and cathode layers, whereby all adjacent cathode layers and anode layers of the stack are electrically insulated from one another by a separator layer. Anode terminal means extend through the capacitor case side wall for electrically connecting a plurality of the anode tabs to one another and providing an anode connection terminal at the exterior of the case. Cathode terminal means extend through or to an encapsulation area of the capacitor case side wall for electrically connecting a plurality of the cathode tabs to one another and providing a cathode connection terminal at the exterior of the case. A connector assembly is electrically attached to the anode connection terminal for making electrical connection with the anode tabs and to the cathode connection terminal for making electrical connection with the cathode tabs. The anode layers are formed of one or more partially through-etched anode sheet bearing an oxide layer and formed with a plurality of punctures therethrough.

15 Claims, 12 Drawing Sheets

U.S. PATENT DOCUMENTS

| | | | |
|---|---|---|---|
| 4,942,501 A | 7/1990 | MacFarlane et al. | 361/523 |
| 4,987,519 A | 1/1991 | Hutchins et al. | 361/518 |
| 5,086,374 A | 2/1992 | MacFarlane et al. | 361/525 |
| 5,131,388 A | 7/1992 | Pless et al. | 128/419 D |
| 5,146,391 A | 9/1992 | MacFarlane et al. | 361/525 |
| 5,153,820 A | 10/1992 | MacFarlane et al. | 361/525 |
| 5,522,851 A | 6/1996 | Fayram | 607/5 |
| 5,562,801 A | 10/1996 | Nulty | 156/643.1 |
| 5,584,890 A | 12/1996 | MacFarlane et al. | 29/25.03 |
| 5,628,801 A | 5/1997 | MacFarlane et al. | 29/25.03 |
| 5,660,737 A | 8/1997 | Elias et al. | 216/6 |
| 5,737,181 A | 4/1998 | Evans | 361/504 |
| 5,748,439 A | 5/1998 | MacFarlane et al. | 361/525 |
| 5,749,911 A | 5/1998 | Westlund | 607/36 |
| 5,801,917 A | 9/1998 | Elias | 361/535 |
| 5,808,857 A | 9/1998 | Stevens | 361/503 |
| 5,814,082 A | 9/1998 | Fayram et al. | 607/5 |
| 5,814,091 A | 9/1998 | Dahlberg et al. | 607/36 |
| 5,862,035 A | 1/1999 | Farahmandi et al. | 361/502 |
| 5,908,151 A | 6/1999 | Elias | 228/110.1 |
| 5,922,215 A | 7/1999 | Pless et al. | 216/6 |
| 5,926,357 A | 7/1999 | Elias et al. | 361/302 |
| 5,968,210 A | 10/1999 | Strange et al. | 29/25.03 |
| 5,983,472 A | 11/1999 | Fayram et al. | 29/25.42 |
| 6,006,133 A | 12/1999 | Lessar et al. | 607/5 |
| 6,009,348 A | 12/1999 | Rorvick et al. | 607/5 |
| 6,032,075 A | 2/2000 | Pignato et al. | 607/5 |
| 6,042,624 A | 3/2000 | Breyen et al. | 29/25.03 |
| 6,238,810 B1 * | 5/2001 | Strange et al. | 205/658 |

* cited by examiner

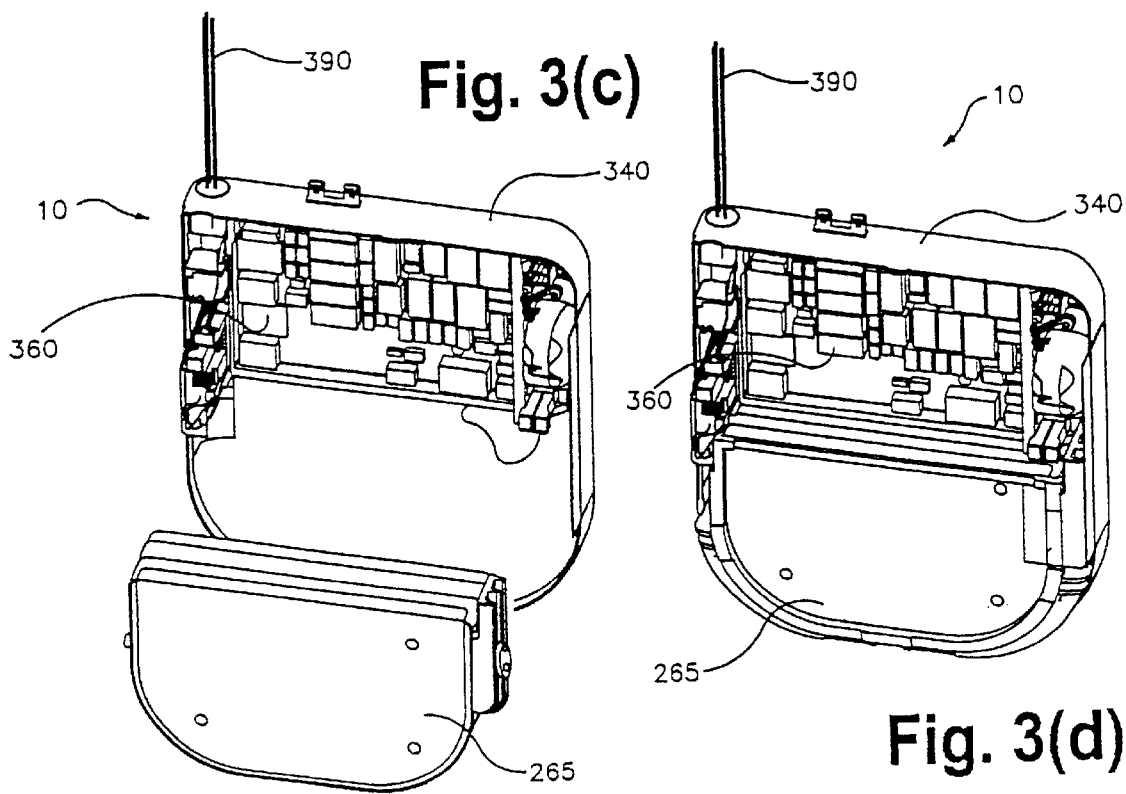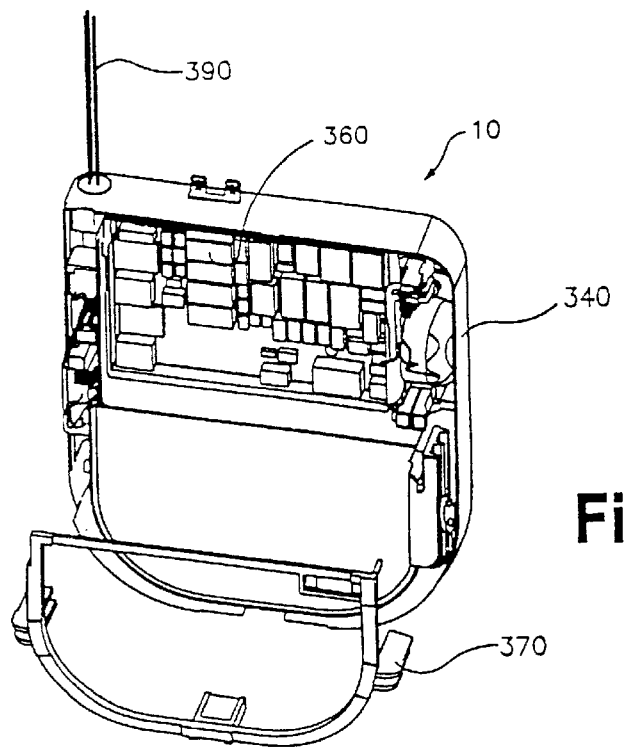

IMPLANTABLE MEDICAL DEVICE HAVING FLAT ELECTROLYTIC CAPACITOR FORMED WITH PARTIALLY THROUGH-ETCHED AND THROUGH-HOLE PUNCTURED ANODE SHEETS

CROSS-REFERENCE TO RELATED APPLICATION

Reference is hereby made to commonly assigned, co-pending U.S. patent application Ser. No. 09/608,576 filed on even date herewith for IMPLANTABLE MEDICAL DEVICE HAVING FLAT ELECTROLYTIC CAPACITOR FORMED WITH NONTHROUGH-ETCHED AND THROUGH-HOLE PUNCTURED ANODE SHEETS filed in the names of Yan et al.

FIELD OF THE INVENTION

This invention relates to implantable medical devices (IMDs) and their various components, including flat electrolytic capacitors for same, and methods of making and using same, particularly such capacitors formed of a plurality of stacked capacitor layers each having anode layers formed of one or a plurality of partially through-etched and through-hole punctured anode sheets.

BACKGROUND OF THE INVENTION

As described in commonly assigned U.S. Pat. No. 6,006,133, a wide variety of IMDs are known in the art. Of particular interest are implantable cardioverter-defibrillators (ICDs) that deliver relatively high energy cardioversion and/or defibrillation shocks to a patient's heart when a malignant tachyarrhythmia, e.g., atrial or ventricular fibrillation, is detected. Current ICDs typically possess single or dual chamber pacing capabilities for treating specified chronic or episodic atrial and/or ventricular bradycardia and tachycardia and were referred to previously as pacemaker/cardioverter/defibrillators (PCDs). Earlier developed automatic implantable defibrillators (AIDs) did not have cardioversion or pacing capabilities. For purposes of the present invention ICDs are understood to encompass all such IMDs having at least high voltage cardioversion and/or defibrillation capabilities.

Energy, volume, thickness and mass are critical features in the design of ICD implantable pulse generators (IPGs) that are coupled to the ICD leads. The battery(s) and high voltage capacitor(s) used to provide and accumulate the energy required for the cardioversion/defibrillation shocks have historically been relatively bulky and expensive. Presently, ICD IPGs typically have a volume of about 40 to about 60 cc, a thickness of about 13 mm to about 16 mm and a mass of approximately 100 grams.

It is desirable to reduce the volume, thickness and mass of such capacitors and ICD IPGs without reducing deliverable energy. Doing so is beneficial to patient comfort and minimizes complications due to erosion of tissue around the ICD IPG. Reductions in size of the capacitors may also allow for the balanced addition of volume to the battery, thereby increasing longevity of the ICD IPG, or balanced addition of new components, thereby adding functionality to the ICD IPG. It is also desirable to provide such ICD IPGs at low cost while retaining the highest level of performance. At the same time, reliability of the capacitors cannot be compromised.

Various types of flat and spiral-wound capacitors are known in the art, some examples of which are described as follows and/or may be found in the patents listed in Table 1 of the above-referenced, commonly assigned, '133 patent. Typically, an electrolytic capacitor is formed with a capacitor case enclosing an etched aluminum anode layer (or "electrode"), an aluminum cathode layer (or "electrode"), and a Kraft paper or fabric gauze spacer or separator impregnated with a solvent based liquid electrolyte interposed therebetween. A layer of aluminum oxide that functions as a dielectric layer is formed on the etched aluminum anode, preferably during passage of electrical current through the anode layer. The electrolyte comprises an ion producing salt that is dissolved in a solvent and provides ionic electrical conductivity between the cathode and the aluminum oxide dielectric layer. The energy of the capacitor is stored in the electromagnetic field generated by opposing electrical charges separated by the aluminum oxide layer disposed on the surface of the anode layer and is proportional to the surface area of the etched aluminum anode layer. Thus, to minimize the overall volume of the capacitor one must maximize anode surface area per unit volume without increasing the capacitor's overall (i.e., external) dimensions. The separator material, anode and cathode layer terminals, internal packaging, electrical interconnections, and alignment features and cathode material further increase the thickness and volume of a capacitor. Consequently, these and other components in a capacitor and the desired capacitance limit the extent to which its physical dimensions may be reduced.

Some ICD IPGs employ commercial photoflash capacitors similar to those described by Troup in "Implantable Cardioverters and Defibrillators," *Current Problems in Cardiology*, Volume XIV, Number 12, December 1989, Year Book Medical Publishers, Chicago, and as described in U.S. Pat. No. 4,254,775. The electrodes or anode and cathodes are wound into anode and cathode layers separated by separator layers of the spiral. Most commercial photoflash capacitors contain a core of separator paper intended to prevent brittle, highly etched aluminum anode foils from fracturing during winding of the anode, cathode and separator layers into a coiled configuration. The cylindrical shape and paper core of commercial photoflash capacitors limits the volumetric packaging efficiency and thickness of an ICD IPG housing made using same.

Flat electrolytic capacitors have also been disclosed in the prior art for general applications as well as for use in ICDs. More recently developed ICD IPGs employ one or more flat high voltage capacitor to overcome some of the packaging and volume disadvantages associated with cylindrical photoflash capacitors. For example, U.S. Pat. No. 5,131,388 discloses a flat capacitor having a plurality of stacked capacitor layers each comprising an "electrode stack sub-assembly". Each capacitor layer contains one or more anode sheet forming an anode layer having an anode tab, a cathode sheet or layer having a cathode tab and a separator for separating the anode layer from the cathode layer. In the '388 patent, the electrode stack assembly of stacked capacitor layers is encased within a non-conductive, polymer envelope that is sealed at its seams and fitted into a chamber of a conductive metal, capacitor case or into a compartment of the ICD IPG housing, and electrical connections with the capacitor anode(s) and cathode(s) are made through feedthroughs extending through the case or compartment wall. The tabs of the anode layers and the cathode layers of all of the capacitor layers of the stack are electrically connected in parallel to form a single capacitor or grouped to form a plurality of capacitors. The aluminum anode layer tabs are gathered together and electrically connected to a feedthrough pin of an anode feedthrough extending through the case or compartment wall. The aluminum cathode layer tabs are gathered together and electrically connected to a feedthrough pin of a cathode feedthrough extending through the case or compartment wall or connected to the electrically conductive capacitor case wall.

Many improvements in the design of flat aluminum electrolytic capacitors for use in ICD IPGs have been disclosed, e.g., those improvements described in "High Energy Density Capacitors for Implantable Defibrillators" presented by P. Lunsmann and D. MacFarlane at *CARTS 96: 16th Capacitor and Resistor Technology Symposium*, Mar. 11–15 1996, and at *CARTS-EUROPE 96: 10th European Passive Components Symposium*, Oct. 7–11 1996, pp. 35–39. Further features of flat electrolytic capacitors for use in ICD IPGs are disclosed in U.S. Pat. Nos. 4,942,501; 5,086,374; 5,146,391; 5,153,820; 5,562,801; 5,584,890; 5,628,801; and 5,748,439, all issued to MacFarlane et al.

Typically, the anode layer of each capacitor layer is formed using a single highly etched anode sheet or a plurality of such anode sheets cut from a highly etched metallic foil. Highly etched aluminum foil has a microscopically contoured, etched surface with a high concentration of pores extending part way through the anode foil along with tunnels extending all the way through the anode foil (through-etched or tunnel-etched) or only with a high concentration of pores extending part way through the anode foil (nonthrough-etched). In either case, such a through-etched or nonthrough-etched anode sheet cut from such highly etched foil exhibit a total surface area much greater than its nominal (length times width) surface area. A surface area coefficient, the ratio of the microscopic true surface area to the macroscopic nominal area, may be as high as 100:1 which advantageously increases capacitance. Through-etched or tunnel-etched anode sheets exhibit a somewhat lower ratio due to the absence of a web or barrier surface closing the tunnel as in nonthrough-etched anode sheets.

After the aluminum foil is etched, the aluminum oxide layer on the etched surface is formed by applying voltage to the foil through an electrolyte such as boric acid or citric acid and water or other solutions familiar to those skilled in the state of the art. Typically, individual anode sheets are punched, stamped or otherwise cut out of the foil in a shape to conform to the capacitor package following formation of the aluminum oxide on the foil. The cut edges around the periphery of the anode sheets are carefully cleaned to remove particulates of anode material that can get caught between the capacitor layers in the electrode stack assembly resulting in a high leakage current or capacitor failure. Anode layers are formed of either a single anode sheet or multiple anode sheets. Capacitor layers are assembled by stacking the anode layer, separator layers, and cathode layer together, and electrode stack assemblies are assembled by stacking a plurality of capacitor layers together, separated by separator layers. The cut edges of the anode and cathode layers and any other exposed aluminum are then reformed in the capacitor during the aging process to reduce leakage current.

Non-through-etched anode sheets are used when only one anode sheet is employed as the anode layer. In order to increase capacitance (and energy density), multiple anode sheets are stacked together to form the multiple sheet anode layer as described above. Through-etched or tunnel-etched anode sheets need to be used in such multiple sheet anode layers to ensure that electrolyte is distributed over all of the aluminum oxide layers of the sandwiched inner anode sheets and to provide a path for ionic communication. But, then the gain in surface area is not as high as that which can be achieved with a like number of stacked nonthrough-etched anode sheets that have a remaining solid section in their center.

For example, the '890 patent discloses the use of an anode layer formed of three anode sheets comprising a highly etched sheet with a solid core in the center and two tunnel-etched anode sheets sandwiching the center sheet. This arrangement is intended to allow the electrolyte and thus the conducting ions to reach the whole surface area of the anode layer, even pores which originate on the inner layer of the foil, yet at the same time the ions are not able to penetrate all the way through the anode layer. More tunnel etched anode sheets can be used in the sandwiched anode layer depending on the desired electrical performance.

Electrical performance of such electrolytic capacitors is effected by the surface area of the anode and cathode layers and also by the resistance associated with the electrolytic capacitor itself, called the equivalent series resistance (ESR). The ESR is a "hypothetical" series resistance that represents all energy losses of an electrolytic capacitor regardless of source. The ESR results in a longer charge time (or larger build factor) and a lower discharge efficiency. Therefore, it is desirable to reduce the ESR to a minimum.

One of the elements of the ESR is the solution resistance inside the pores or tunnels of the anode sheets formed during the electrochemical etching to increase the anode surface area capacitance. The size and depth of a pore and the size of a tunnel through the anode sheet depend on the etching process as well as the oxide formation process. To minimize ESR, the tunnels should be big enough for oxide to grow and long enough for ions to migrate through the anode sheets of the anode layer. In other words, the ideal anode sheet should have pores or tunnels that penetrate through the sheet thickness and are large enough for the electrolyte to flow therethrough. In reality, pores and tunnels vary in size. Narrow tunnels can retard ion transfer, and the pores that are not through-etched tunnels block the paths for ionic migration.

However, as noted above, through-etched tunnels decrease anode layer surface area and reduce the capacitance of a capacitor layer formed with such anode layers in comparison to the capacitance of an equivalent capacitor layer formed using a nonthrough-etched anode layer It is difficult to control the etching parameters to ensure that a minimum number of tunnels having a sufficiently large cross-section to minimize ESR are created so as to maximize capacitance.

High surface area is created during the Electrochemical etching process by dissolving aluminum and forming tunnels or holes. However, the electrochemical tunnel etching is a "random" process, resulting in uncontrollable tunnel site distribution and various tunnel sizes and lengths. As a result, the capacitance of commercial aluminum foils is much lower than that of the ideal foil having site-controllable tunnels with the same size and length.

In order to use multiple anode foil sheets in a "multiple anode sheet configuration" some of the tunnels are through-etched, allowing electrolyte communication on both sides of the foil. In reality, the density of through-etched tunnels is limited in practiced because a high density of through-etched tunnels causes the aluminum foil or sheets cut from the foil to be very brittle. The brittle foil or sheets are very difficult to handle in further processes of forming electrolytic capacitors. Therefore, in practice, the ESR is not sufficiently reduced because of the limited number, size and density of through-etched tunnels extending between the foil or sheet sides.

It is desirable to overcome these problems with providing ionic communication through anode sheets to minimize ESR and maximize surface area.

SUMMARY OF THE INVENTION

The present invention provides for anode layers of electrolytic capacitors that minimize ESR and maximize surface area wherein such capacitors are formed of one or a plurality of stacked capacitor layers each having anode layers formed of one or a plurality of partially through-etched and through-hole punctured anode sheets.

This invention provides paths for electrolyte transfer by forming small through-holes through "partially" through-etched anodes in order that the ESR is reduced and there are more paths for the ions to migrate. The number and size of these through-holes are chosen to reduce the ESR to a minimum while not unnecessarily reducing surface area. In general a minimal number and size of through-hole will be chosen so that the finished capacitor still meets the application requirements. The through-holes need not be round, but that is a convenient shape to use.

In one embodiment employing multiple anode sheets sandwiched together forming an anode layer, the innermost anode sheet is nonthrough etched and not punctured to form a barrier to ion migration or communication through the innermost anode sheet, whereas the outer anode sheets are punctured to enable ion migration and electrolyte distribution to all anode sheet surfaces.

In one embodiment, an exemplary electrolytic capacitor formed in accordance with the present invention comprises an electrode stack assembly and electrolyte located within the interior case chamber of a hermetically sealed capacitor case. The electrode stack assembly comprises a plurality of capacitor layers stacked in registration upon one another, each capacitor layer comprising a cathode layer having a cathode tab, an anode layer comprising at least one anode sheet having an anode tab, and a separator layer located between adjacent anode and cathode layers, whereby all adjacent cathode layers and anode layers of the stack are electrically insulated from one another by a separator layer. Anode terminal means extend through the capacitor case side wall for electrically connecting a plurality of the anode tabs to one another and providing an anode connection terminal at the exterior of the case. Cathode terminal means extend through or to an encapsulation area of the capacitor case side wall for electrically connecting a plurality of the cathode tabs to one another and providing a cathode connection terminal at the exterior of the case. A connector assembly is electrically attached to the anode connection terminal for making electrical connection with the anode tabs and to the cathode connection terminal for making electrical connection with the cathode tabs.

The present invention provides a more controllable method for forming through holes in partially through-hole etched aluminum sheets or foils used to form anode layers. The ESR is thereby reduced while aluminum surface area and capacitance is maintained.

The puncturing method generates more tunnels in aluminum foils used in making aluminum anode sheets for anode layers. However, it also removes the existing tunnels that are created during the electrochemical etching. Since the existing technology can not generate tunnels smaller than those created during the etching process, the net result is surface area reduction and thus capacitance loss. The degree of capacitance loss depends on the hole size and density. However, since more through-holes are created, the ESR is lower.

Since the puncturing process reduces foil capacitance, it should not be overdone. The hole size and density need to be controlled such that the ESR is lowered but the capacitance is not reduced too much.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIGS. 3(a)–3(g) are exploded perspective views of the manner in which the various components of the exemplary ICD IPG of FIGS. 1 and 2, including the electrolytic capacitors of the present invention, are disposed within the housing of the ICD IPG;

DETAILED DESCRIPTION OF THE PREFERRED EMBODIMENTS

Figure 1:
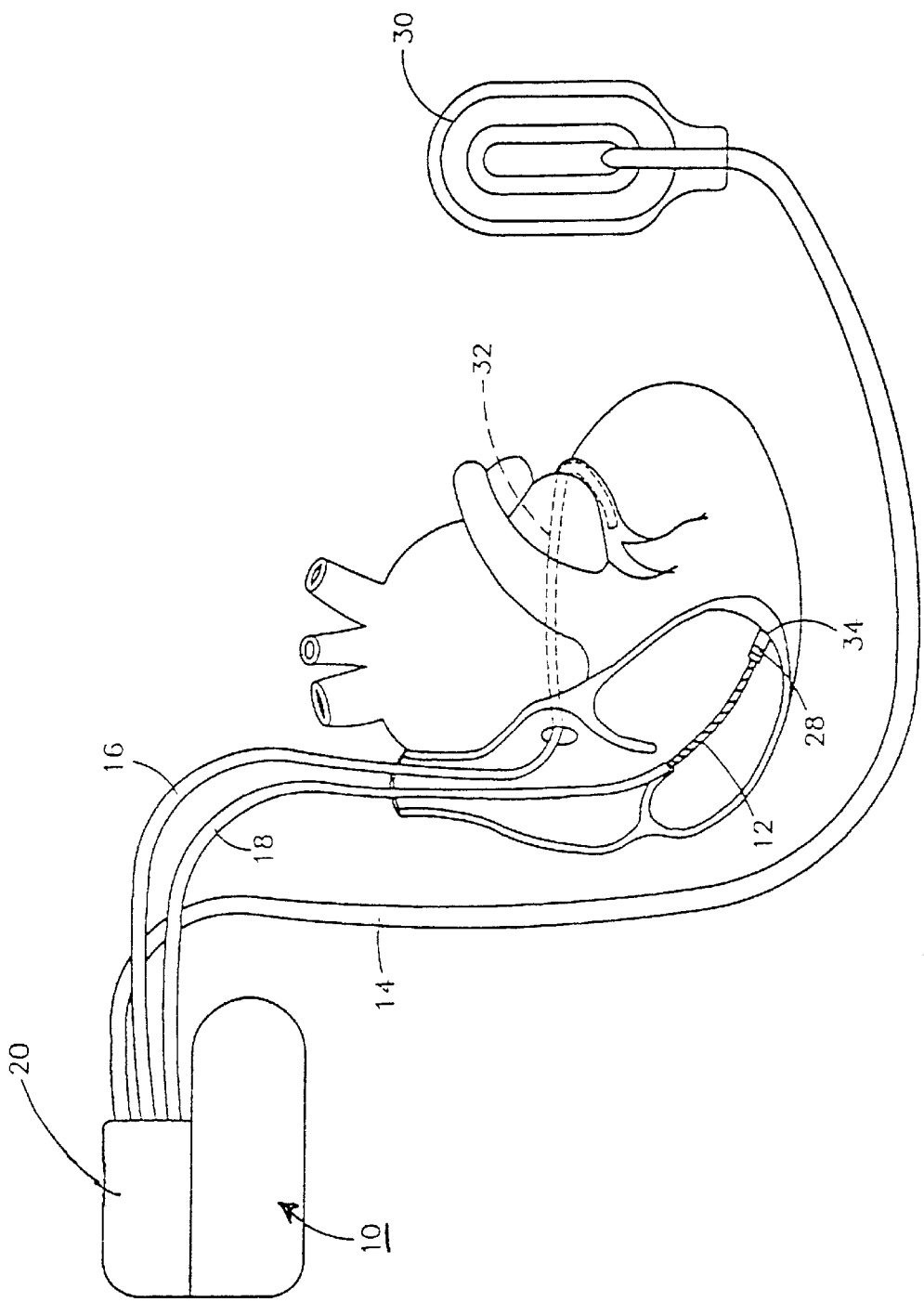
FIG. 1 illustrates the physical components of one exemplary embodiment of an ICD IPG and lead system in which the present invention may be advantageously incorporated.

FIG. 1 illustrates one embodiment of ICD IPG 10 in which the capacitor of the present invention is advantageously incorporated, the associated ICD electrical leads 14, 16 and 18, and their relationship to a human heart 12. The leads are coupled to ICD IPG 10 by means of multi-port connector block 20, which contains separate connector ports for each of the three leads illustrated. Lead 14 is coupled to subcutaneous electrode 30, which is intended to be mounted subcutaneously in the region of the left chest. Lead 16 is a coronary sinus lead employing an elongated coil electrode which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with elongated electrode coil 28 which is located in the right ventricle of the heart. Lead 18 also includes stimulation electrode 34 which takes the form of a helical coil which is screwed into the myocardial tissue of the right ventricle. Lead 18 may also include one or more additional electrodes for near and far field electrogram sensing.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation shock regimens may be also provided, typically between electrode 28 and coronary sinus electrode 32. Alternatively, single pulses may be delivered between electrodes 28 and 30. The particular interconnection of the electrodes to an ICD will depend somewhat on which specific single electrode pair defibrillation shock regimen is believed more likely to be employed.

Figure 2:
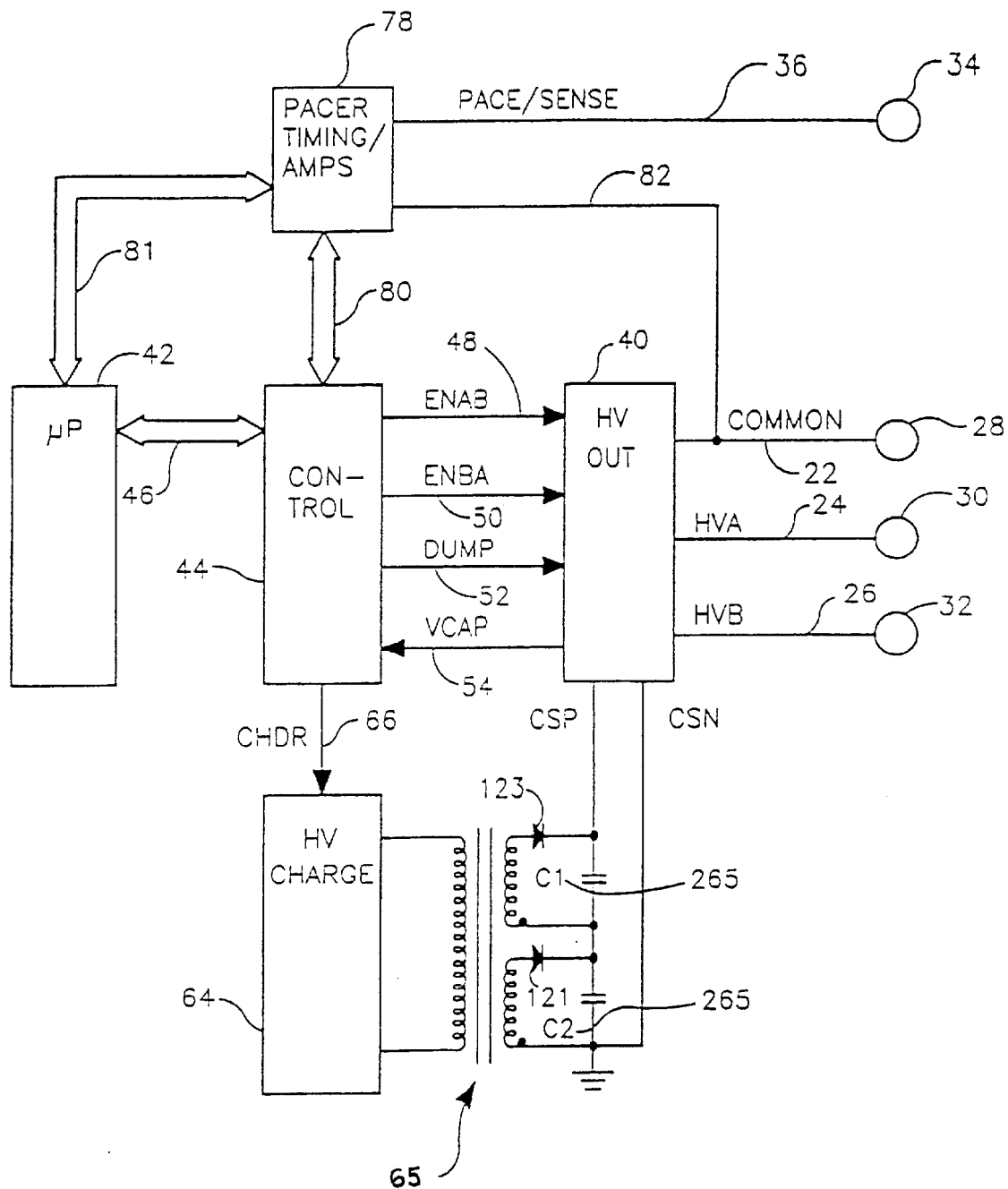
FIG. 2 is a simplified functional block diagram illustrating the interconnection of voltage conversion circuitry with the high voltage capacitors of the present invention with the primary functional components of one type of an ICD.

FIG. 2 is a block diagram illustrating the interconnection of high voltage output circuit 40, high voltage charging circuit 64 and capacitors 265 according to one example of the microcomputer based operating system of the ICD IPG of FIG. 1. As illustrated, the ICD operations are controlled by means of a stored program in microprocessor 42, which performs all necessary computational functions within the ICD. Microprocessor 42 is linked to control circuitry 44 by means of bi-directional data/control bus 46, and thereby controls operation of the output circuitry 40 and the high voltage charging circuitry 64. Pace/sense circuitry 78 awakens microprocessor 42 to perform any necessary mathematical calculations, to perform tachycardia and fibrillation detection procedures and to update the time intervals controlled by the timers in pace/sense circuitry 78 on reprogramming of the ICD operating modes or parameter values or on the occurrence of signals indicative of delivery of cardiac pacing pulses or of the occurrence of cardiac contractions,.

The basic operation and particular structure or components of the exemplary ICD of FIGS. 1 and 2 may correspond to any of the systems known in the art, and the present invention is not dependent upon any particular configuration thereof. The flat aluminum electrolytic capacitor of the present invention may be employed generally in conjunction with the various systems illustrated in the aforementioned '209 patent, or in conjunction with the various systems or components disclosed in the various patents listed in the above-referenced '133 patent.

Control circuitry 44 provides three signals of primary importance to output circuitry 40. Those signals include the first and second control signals discussed above, labeled here as ENAB, line 48, and ENBA, line 50. Also of importance is DUMP line 52 which initiates discharge of the output capacitors and VCAP line 54 which provides a signal indicative of the voltage stored on the output capacitors C1, C2, to control circuitry 44. Defibrillation electrodes 28, 30 and 32 illustrated in FIG. 1, above, are shown coupled to output circuitry 40 by means of conductors 22, 24 and 26. For ease of understanding, those conductors are also labeled as "COMMON", "HVA" and "HVB". However, other configurations are also possible. For example, subcutaneous electrode 30 may be coupled to HVB conductor 26, to allow for a single pulse regimen to be delivered between electrodes 28 and 30. During a logic signal on ENAB, line 48, a cardioversion/defibrillation shock is delivered between electrode 30 and electrode 28. During a logic signal on ENBA, line 50, a cardioversion defibrillation shock is delivered between electrode 32 and electrode 28.

The output circuitry includes a capacitor bank, including capacitors C1 and C2 and diodes 121 and 123, used for delivering defibrillation shocks to the electrodes. Alternatively, the capacitor bank may include a further set of capacitors as depicted in the above referenced '758 application. In FIG. 2, capacitors 265 are illustrated in conjunction with high voltage charging circuitry 64, controlled by the control/timing circuitry 44 by means of CHDR line 66. As illustrated, capacitors 265 are charged by means of a high frequency, high voltage transformer 65. Proper charging polarities are maintained by means of the diodes 121 and 123. VCAP line 54 provides a signal indicative of the voltage on the capacitor bank, and allows for control of the high voltage charging circuitry and for termination of the charging function when the measured voltage equals the programmed charging level.

Pace/sense circuitry 78 includes an R-wave sense amplifier and a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80.

Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

FIGS. 3(a) through 3(g) show perspective views of various components of ICD IPG 10, including one embodiment of the capacitor of the present invention, as those components are placed successively within the housing of ICD IPG 10 formed by right and left hand shields 240 and 350.

Figures 3A, 3B:
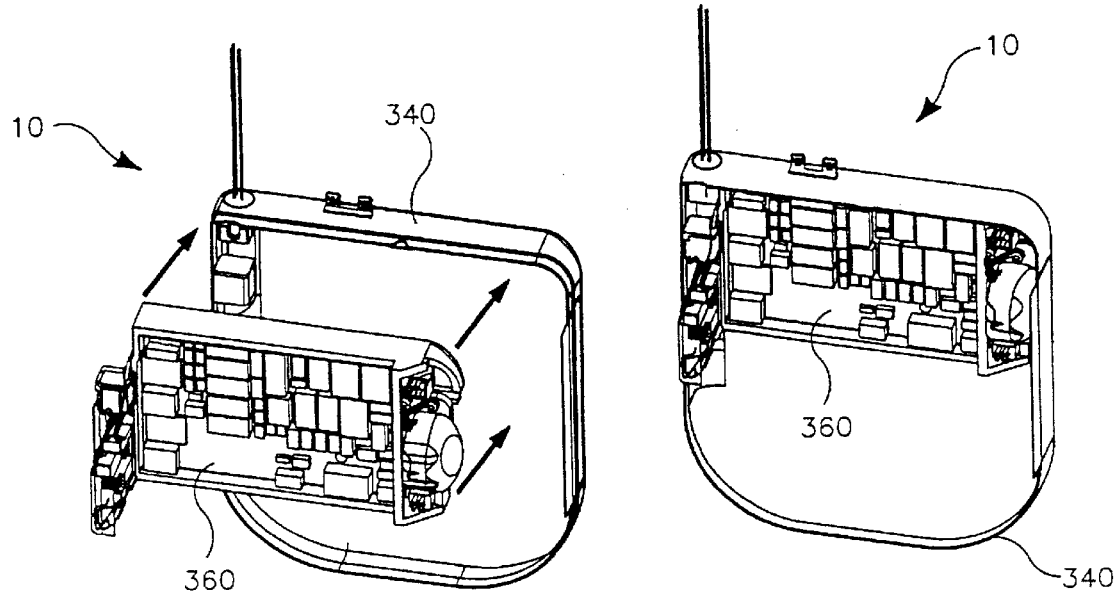
Figure 3F:
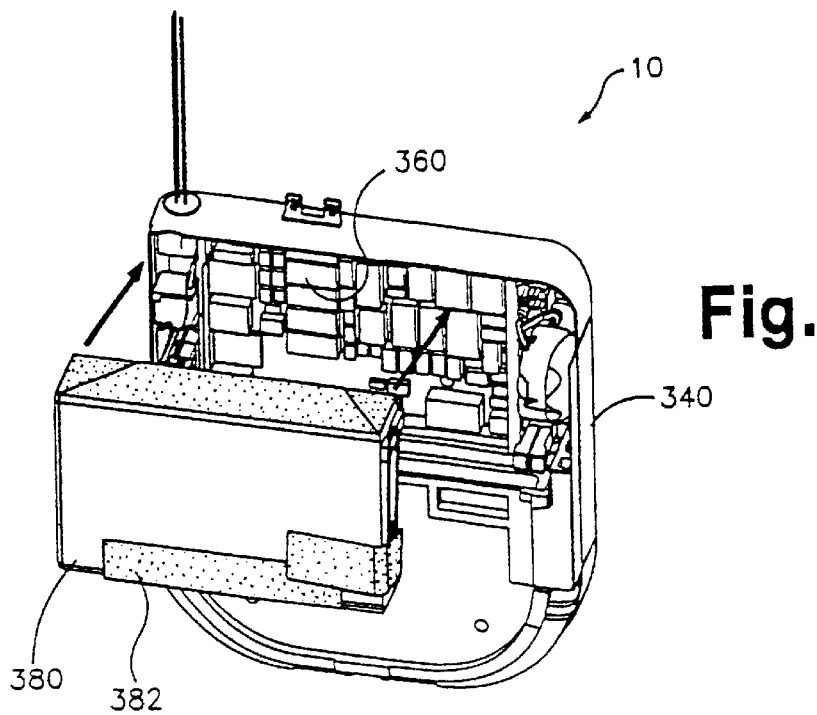
Figure 3G:
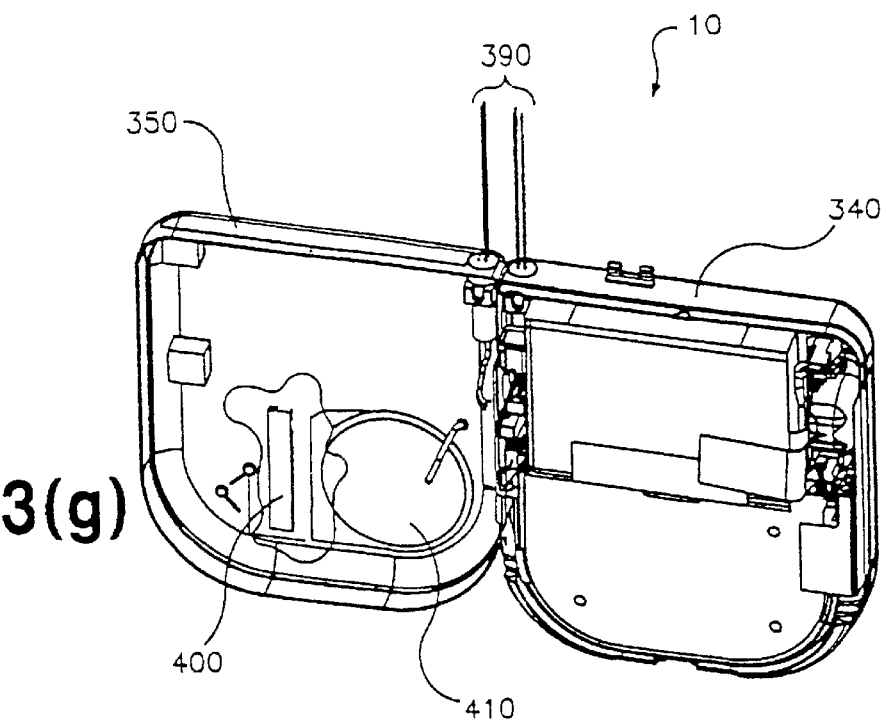

In FIG. 3(a), electronics module 360 is placed in right-hand shield 340 of ICD IPG 10. FIG. 3(b) shows ICD IPG 10 once electronics module 360 has been seated in right-hand shield 340.

FIG. 3(c) shows a pair of capacitors 265 formed as described herein prior to being placed within right-hand shield 340, the capacitors 265 being connected electrically in series by interconnections in electronics module 340. FIG. 3(*d*) shows ICD IPG 10 once the pair of capacitors 265 has been placed within right-hand shield 340. It will be understood that other shapes of capacitors 265 can be inserted into the housing of ICD IPG 10 in the same or similar manner as described here.

FIG. 3(*e*) shows insulator cup 370 prior to its placing atop capacitors 265 in right-hand shield 340. FIG. 3(*f*) shows electrochemical cell or battery 380 having insulator 382 disposed around battery 380 prior to placing it in shield 340. Battery 380 provides the electrical energy required to charge and re-charge capacitors 265, and also powers electronics module 360. Battery 380 may take any of the forms employed in the prior art to provide cardioversion/defibrillation energy, some of which are identified in above referenced, commonly assigned, '133 patent.

FIG. 3(*h*) shows ICD IPG 10 having left-hand shield 350 connected to right-hand shield 340 and feedthrough 390 projecting upwardly from both shield halves. Activity sensor 400 and patient alert apparatus 410 are shown disposed on the side lower portion of left-hand shield 350. Left-hand shield 350 and right-hand shield 340 are subsequently closed and hermetically sealed (not shown in the figures).

Figure 4:
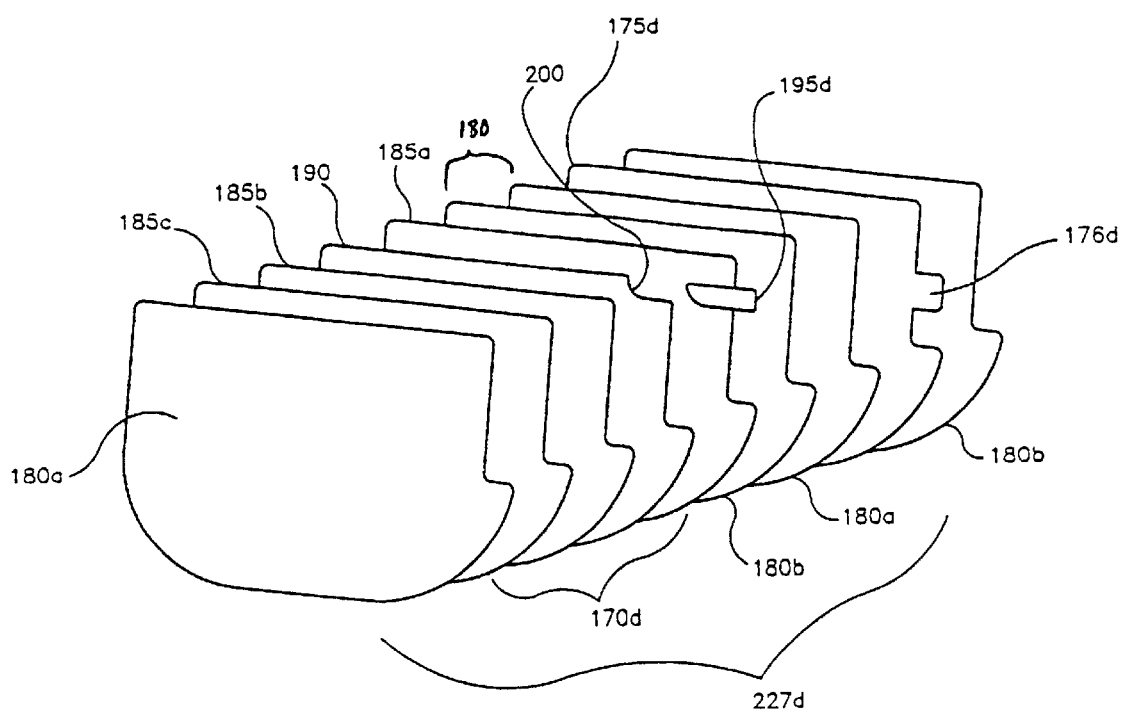
FIG. 4 is an exploded view of one embodiment of a single capacitor layer of an electrolytic capacitor incorporating the present invention.

FIG. 4 shows an exploded view of one embodiment of an anode-cathode sub-assembly or capacitor layer 227 of capacitor 265. The capacitor design described herein employs a stacked configuration of a plurality of capacitor layers 227 as further described below with respect to FIG. 5. Each capacitor layer 227 comprises alternating substantially rectangular-shaped anode layers 170 and cathode layers 175, with a substantially rectangular-shaped separator layer 180 being interposed therebetween. The shapes of anode layers 170, cathode layers 175 and separator layers 180 are primarily a matter of design choice, and are dictated largely by the shape or configuration of case 90 within which those layers are ultimately disposed. Anode layers 170, cathode layers 175 and separator layers 180 may assume any arbitrary shape to optimize packaging efficiency.

Exemplary anode layer 170*d* most preferably comprises a plurality of non-notched anode sheets 185 designated 185*a*, 185*b*, 185*c*, notched anode sheet 190 including anode tab notch 200, and anode tab 195 coupled to anode sheet 185*a*. It will be understood that anode layer 170*d* shown in FIG. 4 is but one possible embodiment of an anode layer 170. Exemplary cathode layer 175*d* most preferably is formed of a single sheet of aluminum foil and has cathode tab 176 formed integral thereto and projecting from the periphery thereof.

Individual anode sheets 185/190 are typically somewhat stiff and formed of high-purity aluminum processed by etching to achieve high capacitance per unit area. Thin anode foils are preferred, especially if they substantially maintain or increase specific capacitance while reducing the thickness of the electrode stack assembly 225, or maintain the thickness of electrode stack assembly 225 while increasing overall capacitance. For example, it is contemplated that individual anode sheets 185/190 have a thickness of between about 10 micrometers and about 500 micrometers.

Cathode layers 175 are preferably formed of a single sheet cut from high purity, flexible, aluminum foil. Cathode layers 175 are most preferably formed of cathode foil having high surface area (i.e., highly etched cathode foil), high specific capacitance (preferably at least 200 microfarads/cm$^2$, and at least 250 microfarads/cm$^2$ when fresh), a thickness of about 30 micrometers, a cleanliness of about 1.0 mg/m$^2$ respecting projected area maximum chloride contamination, and a purity which may be less than corresponding to the starting foil material from which anode foil is made. The cathode foil preferably has an initial purity of at least 99% aluminum, and more preferably yet of about 99.4% aluminum, a final thickness of about 30 micrometers, and an initial specific capacitance of about 250 microfarads per square centimeter. In other embodiments, cathode foil has a specific capacitance ranging between about 100 and about 500 microfarads/cm$^2$, and a thickness ranging between about 10 and about 150 micrometers.

It is generally preferred that the specific capacitance of the cathode foil be as high as possible, and that cathode layer 175 be as thin as possible. For example, it is contemplated that individual cathode layers 175 have a specific capacitance of about 100–1,000 microfarads/cm$^2$. Suitable cathode foils are commercially available on a widespread basis. In still other embodiments, cathode foil is formed of materials or metals in addition to aluminum, aluminum alloys and "pure" aluminum.

Separator layer sheets 180*a* and 180*b* and outer separator layers of the electrode stack assembly 225 (FIG. 8) formed from a plurality of stacked capacitor layers 227 are most preferably made from a roll or sheet of separator material. Separator layers 180 are preferably cut slightly larger than anode layers 170 and cathode layers 175 to accommodate misalignment during the stacking of layers, to prevent subsequent shorting between anode and cathode layers, and to otherwise ensure that a physical barrier is disposed between the anodes and the cathodes of the finished capacitor.

In one preferred embodiment of the capacitor layer 227 as depicted in FIG. 4, two individual separator layer sheets 180*a* and 180*b* form the separator layer 180 that is disposed between each anode layer 170 and cathode layer 175. Further single separator layer sheets 180*a* and 180*b* are disposed against the outer surfaces of the anode sheet 185*c* and the cathode layer 175*d*. When the sub-assemblies are stacked, the outermost single separator layer sheets 180*a* and 180*b* bear against adjacent outermost single separator layer sheets 180*b* and 180*a*, respectively, of adjacent capacitor layers so that two sheet separator layers 180 separate all adjacent cathode and anode layers of an electrode stack assembly 225.

It is preferred that separator layer sheets 180*a* and 180*b* and exterior separator layers between the electrode stack assembly and the case and cover be formed of a material that: (a) is chemically inert; (b) is chemically compatible with the selected electrolyte; (c) may be impregnated with the electrolyte to produce a low resistance path between adjoining anode and cathode layers, and (d) physically separates adjoining anode and cathode layers. In one preferred embodiment, separator material is a pure cellulose, very low halide or chloride content Kraft paper having a thickness of about 0.0005 inches, a density of about 1.06 grams/cm$^3$, a dielectric strength of 1,400 Volts AC per 0.001 inches thickness, and a low number of conducting paths (about 0.4/ft$^2$ or less). Separator layer sheets 180*a* and 180*b* and outer separator layers 165*a* and 165*b* may also be formed of materials other than Kraft paper, such as Manila paper, porous polymeric materials or fabric gauze materials. In such capacitor stacks formed of a plurality of capacitor layers, a liquid electrolyte saturates or wets separator layers 180 and is disposed within the capacitor interior case chamber.

It will be understood by those skilled in the art that the precise number of capacitor layers 227 selected for use in a electrode stack assembly 225 will depend upon the energy density, volume, voltage, current, energy output and other requirements placed upon capacitor 265. Similarly, it will be understood by those skilled in the art that the precise number of notched anode sheets 190 and un-notched anode sheets 185, anode tabs 195, anode layers 170, cathode layers 175 and separator layers 180 selected for use in a given embodiment of capacitor layer 227 will depend upon the energy density, volume, voltage, current, energy output and other requirements placed upon capacitor 265. It will now become apparent that a virtually unlimited number of combinations and permutations respecting the number of capacitor layers 227, and the number of notched anode sheets 190 and un-notched anode sheets 185 forming anode layer 170, anode layers 170, anode tabs 195, cathode layers 175 and separator layers 180 disposed within each capacitor layer 227, may be selected according to the particular requirements of capacitor 265.

Figure 5:
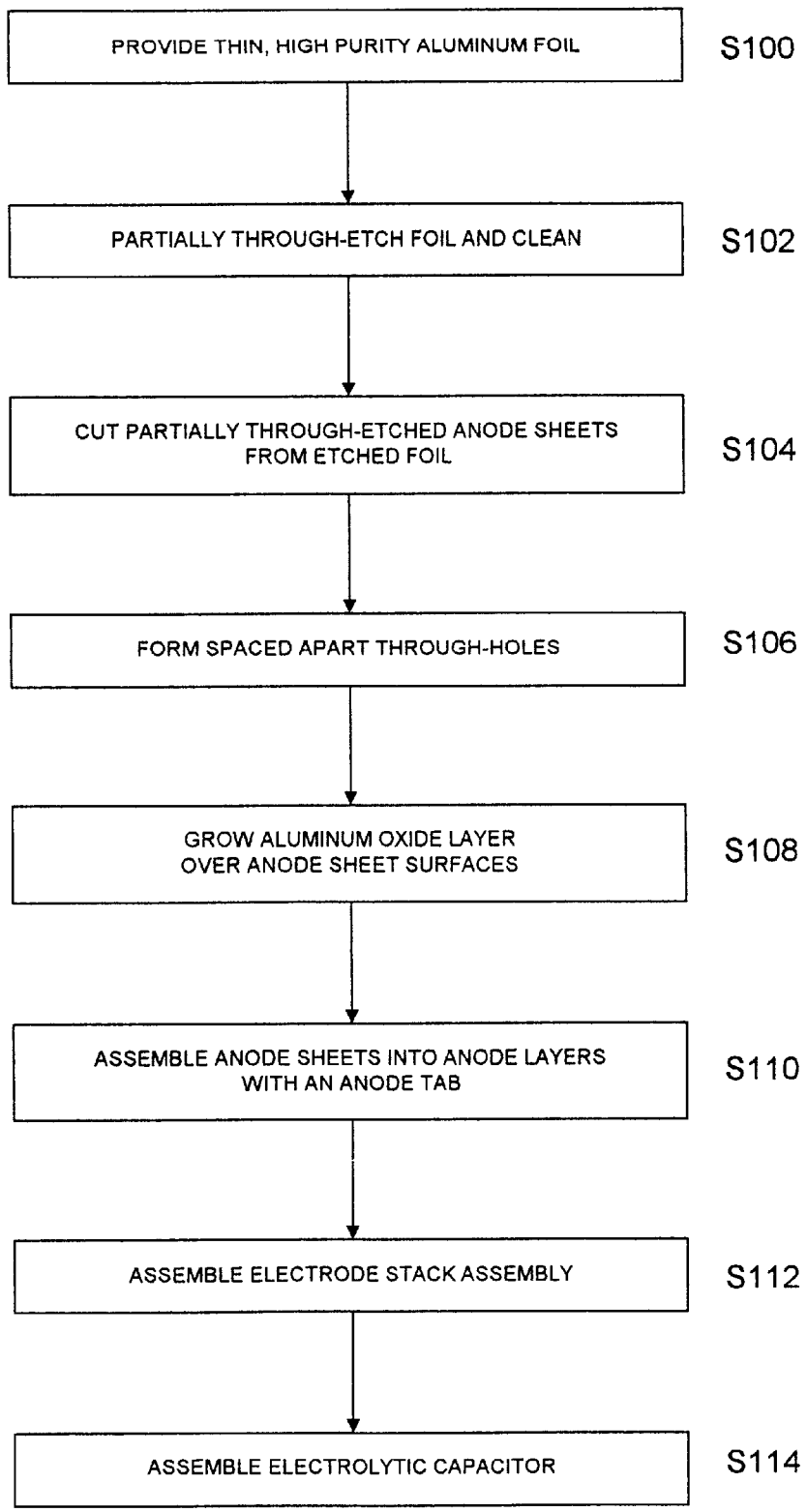
FIG. 5 is a flow chart illustrating the steps of forming an electrolytic capacitor in accordance with the invention.

FIG. 5 depicts the method of forming anode sheets having through holes and then using the anode sheets to fabricate an electrolytic capacitor. The first thin aluminum foil of the type described above is provided in step S100, etched in step S102, and cut into anode sheets 185/190 shown in FIG. 6(a) in step S104. The anode foil is at least partially through-etched in step S102, has a high specific capacitance (at least about 0.3, at least about 0.5 or most preferably at least about 0.8 microfarads/cm$^2$), has a dielectric withstand parameter of at least 425 Volts DC, a thickness ranging between about 50 and about 200 micrometers, and a cleanliness of about 1.0 mg/m$^2$ respecting projected area maximum chloride contamination. The anode foil preferably has a rated surge voltage of 390 Volts, an initial purity of about 99.99% aluminum, a final thickness of about 104 micrometers, plus or minus about five micrometers, and a specific capacitance of about 0.8 microfarads per square centimeter. Suitable anode foils etched to specification are commercially available on a widespread basis.

The anode and cathode sheets are most preferably cut to shape using dies having low wall-to-wall clearance, where inter-wall spacing between the substantially vertically-oriented corresponding walls of the punch and die is most preferably on the order of about 6 millionths of an inch per side. Larger or smaller inter-wall spacings between the substantially vertically-oriented corresponding walls of the punch and cavity, such as about 2–12 millionths of an inch may also be employed but are less preferred. The tabs 176 and 195 and separator layers 180 are also preferably cut from aluminum foil and Kraft paper, respectively, in the same manner.

Such low clearance results in smooth, burr free edges being formed along the peripheries of anode sheets 185 and 190, tabs 176 and 195, cathode layers 175 and separator layers 180. Smooth, burr free edges on the walls of the dies have been discovered to be critical respecting reliable performance of a capacitor. The presence of burrs along the peripheries of anode sheets 185 and 190, anode tabs 195, cathode layers 175 and separator layers 180 may result in short circuit and failure of the capacitor. The means by which anode foil, cathode foil and separator materials are cut or formed may have a significant impact on the lack or presence of burrs and other cutting debris disposed about the peripheries of the formed or cut members. The use of low clearance dies produces an edge superior to the edge produced by other cutting methods, such as steel rule dies. The shape, flexibility and speed of a low clearance die have been discovered to be superior to those achieved by laser or blade cutting. Other methods of cutting or forming anode sheets 185 and 190, anode tab 195, cathode layers 175 and separator layers 180 include, but are not limited to, steel rule die cutting, laser cutting, water jet cutting and blade cutting. Further details relating to preferred methods of cutting the anode foil to form anode sheets and sandwiching anode sheets together to form an anode layer 170 are set forth in the above-referenced, commonly assigned, '133 patent.

Figure 6A:
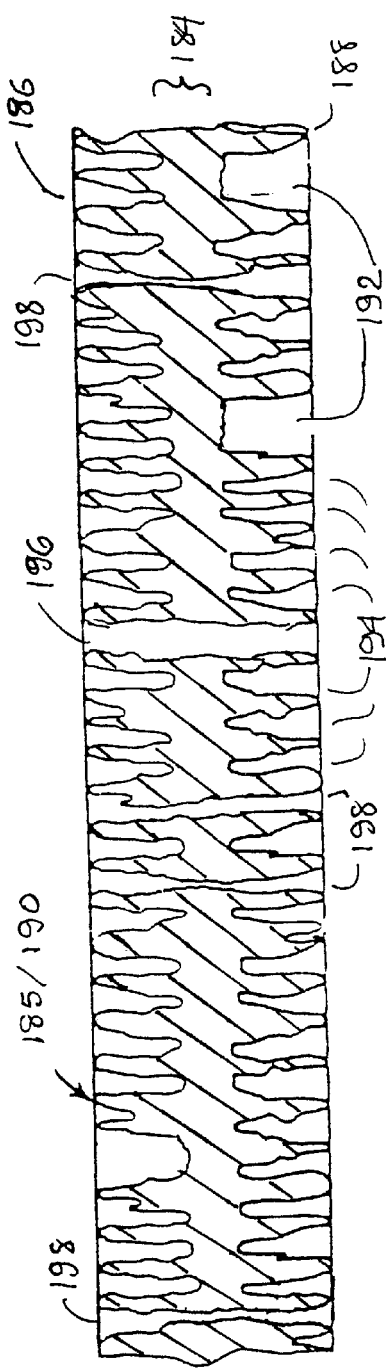
FIG. 6(a) is a side cross-section view of partially through-etched anode sheet prior to puncturing in accordance with the present invention.

In FIG. 6(a), the partially through-etched anode sheet 185/190 has opposed major anode sheet surfaces 186 and 188 that are highly etched to form certain pores 192, 194 extending part way through the thickness of anode sheet 185/190 to a sheet web or core 184 and certain through-etched tunnels 196, 198 extending all the way through the sheet web thickness and core 184. The large pores 192, small pores 194, large cross-section tunnels 196, and small cross-section tunnels 198 provide enhanced surface area in comparison to the planar sheet surfaces 186, 188 prior to etching. However, some surface area potential is lost by virtue of overly large pores 192 and tunnels 196. Conversely, ESR is increased by small tunnels 198 that impede electrolyte and ion passage therethrough.

Figure 6B:
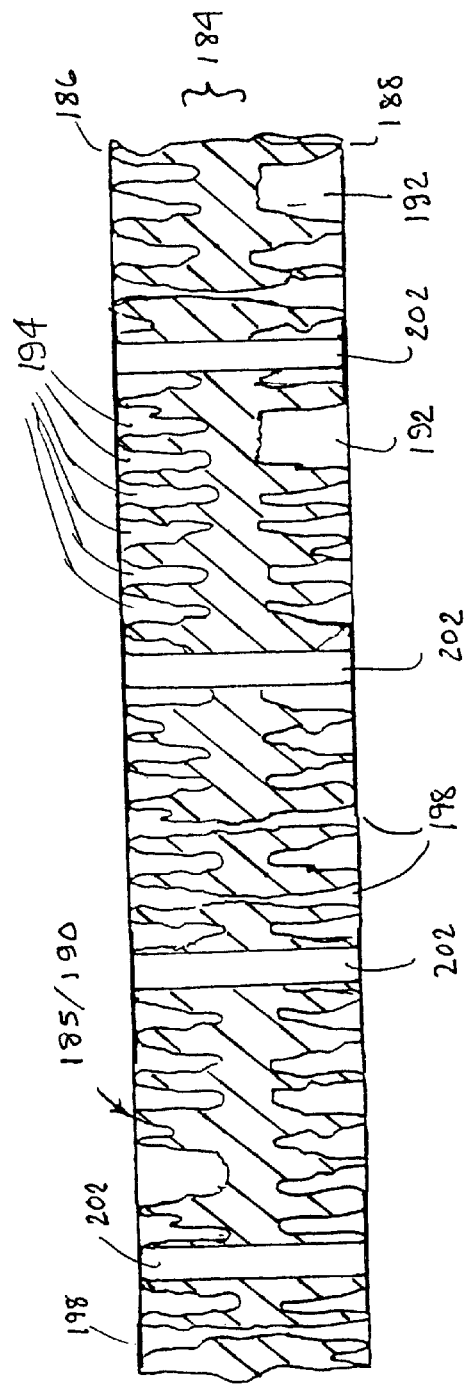
FIG. 6(b) is a side cross-section view of the partially through-etched anode sheet of FIG. 6(a) following puncturing in accordance with the present invention for use in the capacitor layer of FIGS. 4 and 6(c)

In accordance with the present invention, a degree of through etching of the aluminum foil is conducted in step S102 that provides for a majority of small pores 194 and small tunnels 198 so that surface area and corresponding capacitance are maximized and large pores 192 and tunnels 196 are minimized, whereby the ESR may be less than optimal. In accordance with step S106, a plurality of through-holes 202 depicted in FIG. 6(b) are then formed that extend between the first and second opposed major surfaces 186 and 188 and through the anode sheet thickness and core 184. Preferably, the through holes 202 are preferably uniformly sized and uniformly spaced apart. The number per unit area and size of these through-holes 202 are chosen to reduce the ESR to a minimum while not unnecessarily reducing surface area. In general a minimal number, spacing apart, and size of through-hole will be chosen so that the finished capacitor still meets the application requirements.

The through-holes are preferably formed by any puncturing process e.g., by punching, mechanically drilling, laser boring, etc. Through-holes need not be round, but that is a convenient shape to use.

Then, in step S108, the aluminum oxide dielectric layer is grown over the pores 192, 194, the tunnels 196, 198, the through holes 202 and the anode sheet cut edges in a manner known in the art. The anode sheets 185/190 are assembled together in step S110 to form anode layers 170, following the process and using the equipment described in the above referenced, commonly assigned, '133 patent.

Figure 6C:
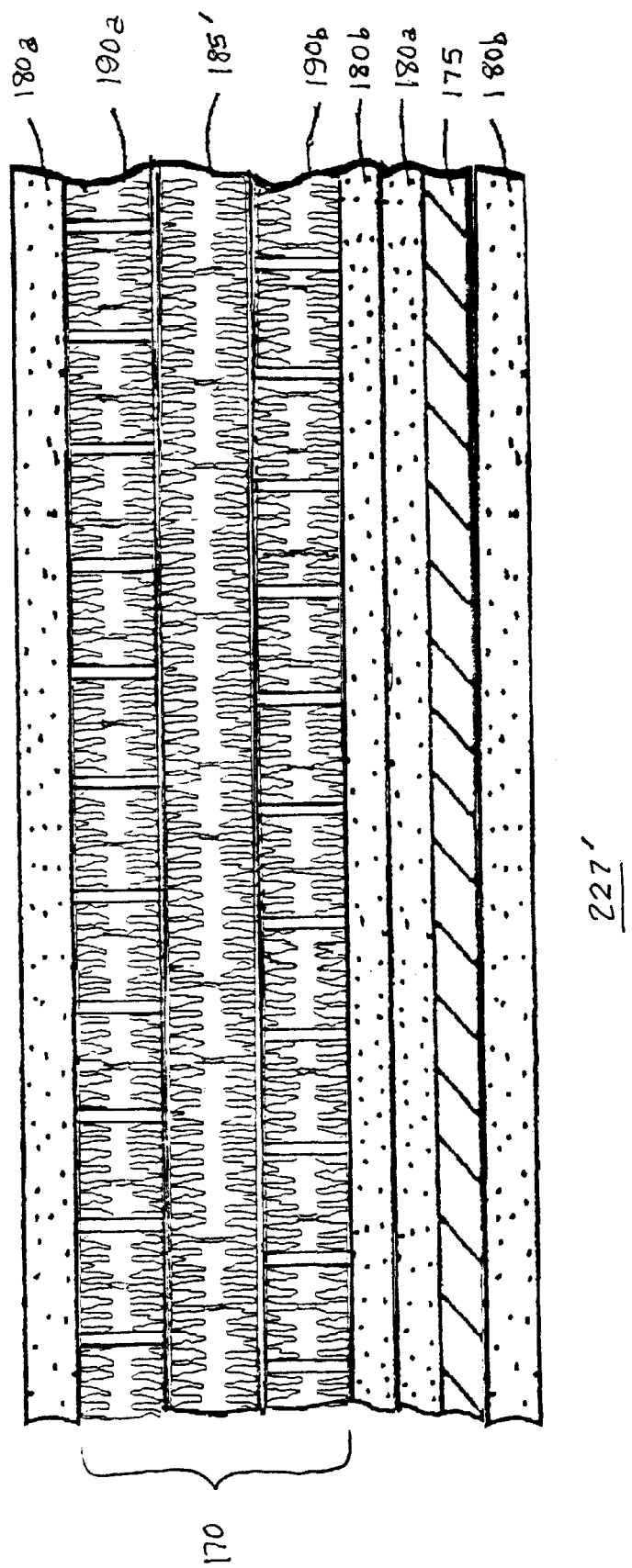
FIG. 6(c) is a side cross-section view of a particular embodiment of a single capacitor layer of an electrolytic capacitor incorporating the partially through-etched anode sheet of FIG. 6(a) in conjunction with through-hole punctured, partially through-etched, anode sheets of FIG. 6(b)

In one fabrication method following these steps, all of the partially through-etched anode sheets 185a–185c and 190 forming into the anode layer 170d of the capacitor layer 227d illustrated in FIG. 4 are through-hole punctured in accordance with step S106. FIG. 6(c) illustrates a variation of a capacitor layer 227' formed in steps S100–S110 that employs through-hole punctured anode sheets 190a and 190b illustrated in FIG. 6(b) assembled in a sandwich or stack on either side of a partially through-etched anode sheet 185' of FIG. 6(a). The partially through-etched anode sheet 185' is not punctured in accordance with step S106. The through-holes in the outer through-hole punctured anode sheets 190a and 190b ensure that electrolyte reaches the major opposed surfaces of the innermost partially through-etched anode sheet 185'.

In this illustrated example of FIG. 6(c), a tab (not shown) is attached to the centrally disposed partially through-etched anode sheet 185', and the through-hole punctured anode sheets 190a and 190b are identified as notched anode sheets to accommodate the tab. Other selections of tabbed and notched anode sheets 185/190 may be substituted for the illustrated selection.

Moreover, any number of outer through-hole punctured anode sheets 185/190 of FIG. 6(b) can be stacked in equal or unequal numbers on either side of the centrally disposed partially through-etched anode sheet 185' to form an anode layer 170.

Figure 6D:
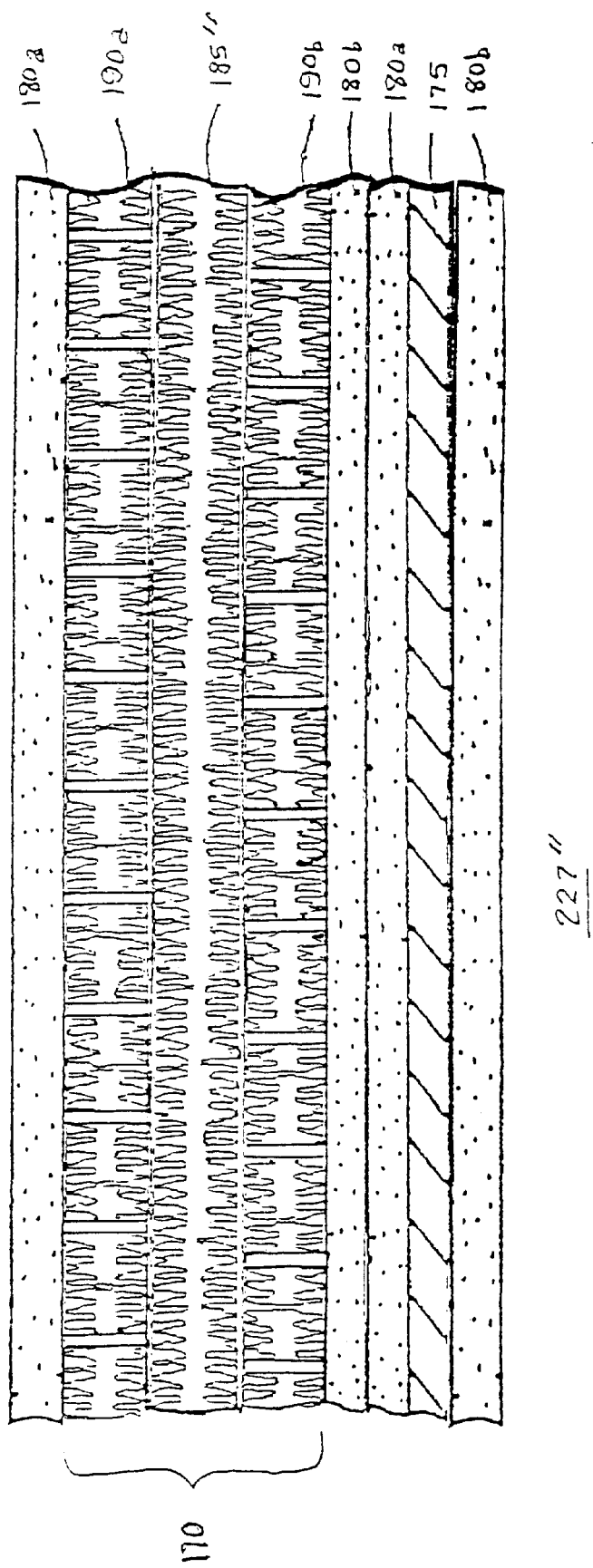
FIG. 6(d) is a side cross-section view of a further particular embodiment of a single capacitor layer of an electrolytic capacitor incorporating a nonthrough-etched anode sheet in conjunction with through-hole punctured, partially through-etched, anode sheets of FIG. 6(b)

In addition, the innermost anode sheet 185" may be nonthrough-hole etched as illustrated in FIG. 6(d). In this example, a second aluminum foil is provided in step S100 and is nonthrough-hole etched and cut in steps parallel to steps S102–S106 of FIG. 5.

Figure 7:
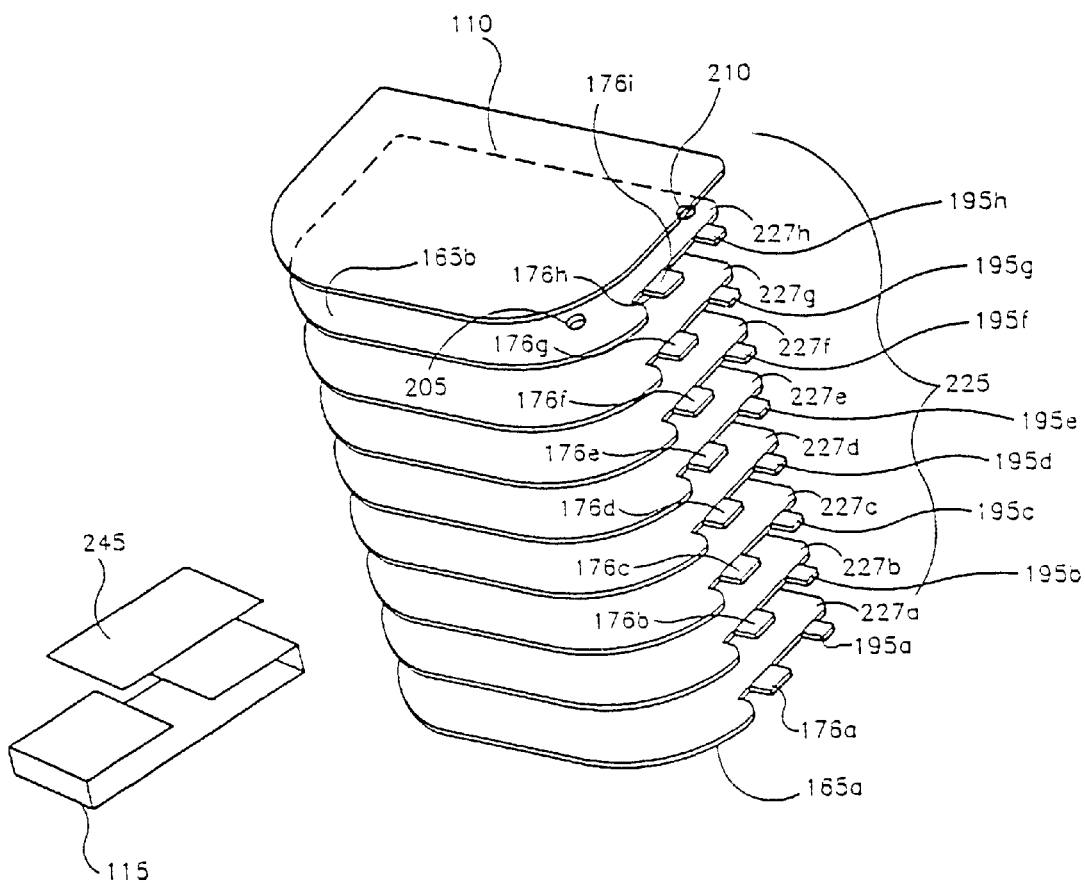
FIG. 7 is an exploded top perspective view of one embodiment of a series of capacitor layers incorporating the present invention assembled into a electrode stack assembly of an electrolytic capacitor.
Figure 8:
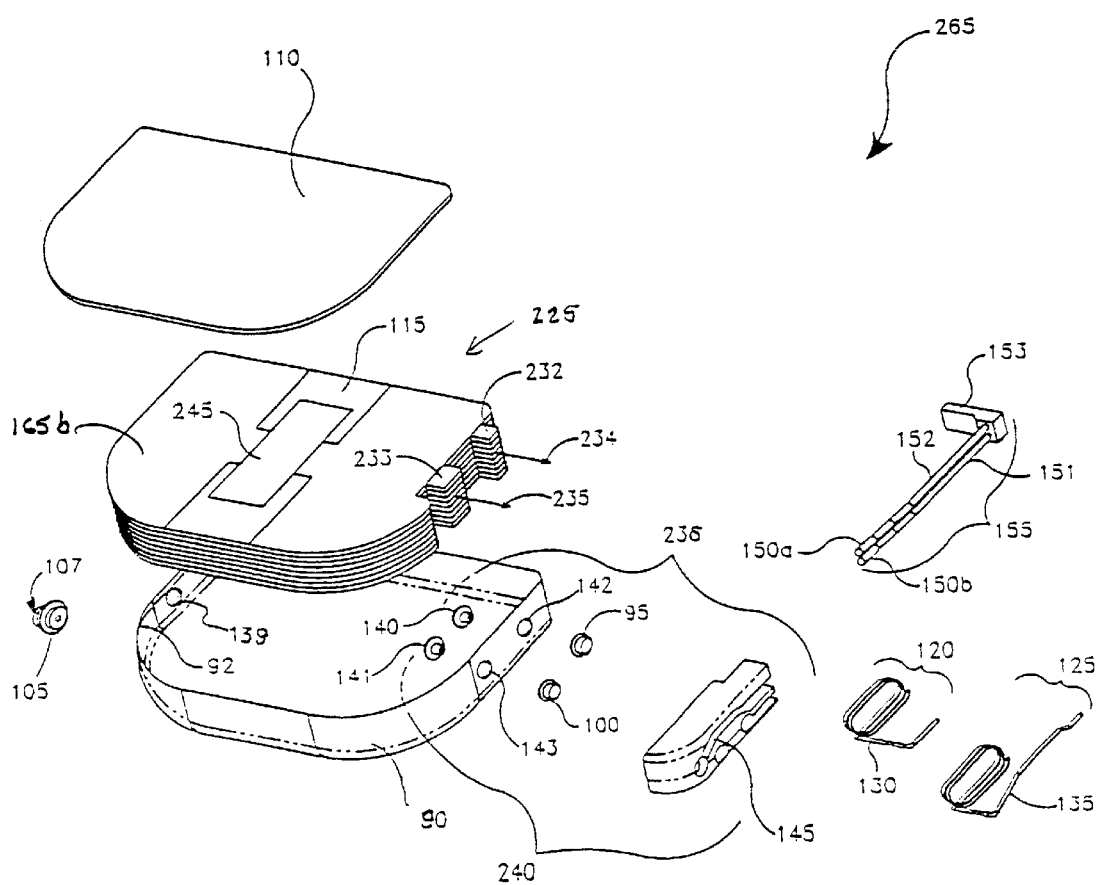
FIG. 8 is an exploded top perspective view of the components of one embodiment of an electrolytic capacitor fabricated in accordance with the final step of FIG. 5 and incorporating the present invention.

FIG. 7 illustrates the formation of the electrode stack assembly 225 in accordance with step S112 in relation to a capacitor case cover 110 for a capacitor case 90 illustrated in FIG. 8. The electrode stack assembly 225 comprises a plurality of capacitor layers 227a–227h formed as described above and having anode tabs 195a–195h and cathode tabs 176a–176h. The voltage developed across each capacitor layer disposed within electrode stack assembly 225 most preferably ranges between about 360 and about 390 Volts DC. As described below, the various anode sub-assemblies of electrode stack assembly 225 are typically connected in parallel electrically, as are the various cathode layers of electrode stack assembly 225. Electrode stack assembly 225 shown in FIG. 7 is merely illustrative, and does not limit the scope of the present invention in any way respecting the number or combination of anode layers 170, cathode layers 175, separator layers 180, anode tabs 195, cathode tabs 176, and so on. The number of electrode components is instead determined according to the total capacitance required, the total area of each layer, the specific capacitance of the foil employed and other factors.

The use of the through-holes of the present invention facilitates using a multiple number of anode sheets 185/190 employed in each anode layer 170 permitting the fabrication of capacitors having the same layer area but nearly continuously varying different and selectable total capacitances that a user may determine by increasing or decreasing the number of anode sheets 185/190 included in selected anode layers 170 (as opposed to adding or subtracting full capacitor layers 227 from electrode stack assembly 225 to thereby change the total capacitance).

The capacitor layers 227a 227h and the outer paper layers 165a and 165b are stacked, and outer wrap 115 is folded over the top of electrode stack assembly 225 in step S112. Wrapping tape 245 is then holds outer wrap 115 in place and secures the various components of electrode stack assembly 225 together. Outer wrap 115 is most preferably die cut from separator material described above, but may be formed from a wide range of other suitable materials such as polymeric materials, aluminum, suitable heat shrink materials, suitable rubberized materials and synthetic equivalents or derivatives thereof, and the like. Wrapping tape 245 is most preferably cut from a polypropylene-backed acrylic adhesive tape, but may also be replaced by a staple, an ultrasonic paper joint or weld, suitable adhesives other than acrylic adhesive, suitable tape other than polypropylene-backed tape, a hook and corresponding clasp and so on. Usable alternatives to outer wrap 115 and wrapping tape 245 and various stacking and registration processes by which electrode stack assembly 225 is most preferably made are not material to the present invention and are disclosed in the above-referenced, commonly assigned, '133 patent.

FIG. 8 shows an exploded top perspective view of one embodiment of an exemplary, case neutral, electrolytic capacitor 265 employing the electrode stack assembly 225 of FIGS. 7 therein and the electrical connections made to the gathered anode and cathode tabs 232 and 233. This embodiment includes anode feedthrough 120 and cathode feedthrough 125 most preferably having coiled basal portions 121 and 126, respectively. Feedthroughs 120 and 125 provide electrical feedthrough terminals for capacitor 265 and gather gathered anode tabs 232 and gathered cathode tabs 233 within basal portions 121 and 126 for electrical and mechanical interconnection.

Feedthrough wire is first provided and trimmed to length for construction of feedthroughs 120 and 125. One end of the trimmed wire is coiled such that its inside diameter or dimension is slightly larger than the diameter or dimension required to encircle gathered anode tabs 232 or gathered cathode tabs 233. Gathered anode tabs 232 are next gathered, or brought together in a bundle by crimping, and inside diameter 131 of anode feedthrough coil assembly 120 is placed over gathered anode tabs 232 such that anode feedthrough pin 130 extends outwardly away from the base of gathered anode tabs 232. Similarly, gathered cathode tabs 233 are gathered and inside diameter 136 of cathode feedthrough coil assembly 125 is placed over gathered cathode tabs 233 such that cathode feedthrough pin 135 extends outwardly away from the base of cathode tab 233. Coiled basal portions 121 and 126 of anode and cathode feedthroughs 120 and 125 are then most preferably crimped onto anode and cathode tabs 232 and 233, followed by trimming the distal ends thereof, most preferably such that the crimps so formed are oriented substantially perpendicular to imaginary axes 234 and 235 of gathered anode and cathode tabs 232 and 233. Trimming the distal ends may also, but less preferably, be accomplished at other non-perpendicular angles respecting imaginary axes 234 and 235.

In some preferred methods, a crimping force is applied to feedthrough coils 121 and 126 and tabs 232 and 233 throughout a subsequent preferred welding step. In one method, it is preferred that the crimped anode and cathode feedthroughs be laser or ultrasonically welded along the top portion of the trimmed edge of the distal ends to anode and cathode tab 232 and 233. Following welding of feedthroughs 120 and 125 to gathered anode tabs 232 and gathered cathode tabs 233, respectively, pins 130 and 135 are bent for insertion through feedthrough holes 142 and 143 of case 90.

Many different embodiments of the feedthroughs and means for connecting the feedthrough pins to anode and cathode tabs exist other than those shown explicitly in the figures and are described in the above-referenced, commonly assigned, '133 patent.

A case sub-assembly is also created from case 90, anode ferrule 95, cathode ferrule 100, and fill port ferrule 105 are first provided. In a preferred embodiment of capacitor 265, the case 90 and cover 110 are formed of aluminum. In other embodiments, case 90 or cover 110 may be formed of any other suitable corrosion-resistant metal such as titanium or stainless steel, or may alternatively be formed of a suitable plastic, polymeric material or ceramic. The anode ferrule 95 and cathode ferrule 100 are welded to the aluminum case side wall to fit around anode and cathode feedthrough ferrule holes 142 and 143, and a fill port ferrule is welded to the case side wall around a fill port hole 139. The welding steps form no part of the present invention and various ways of doing so are disclosed in detail in the above-referenced, commonly assigned, '133 patent.

Wire guides 140 and 141 fit within center holes of ferrules 95 and 100 respectively and receive, center, and electrically insulate anode and cathode pins 130 and 135 from the case 90, anode ferrule 95, and cathode ferrule 100. The formation and assembly of the wire guides 140, 141 with the ferrules 95, 100 and cathode pins 130, 135 form no part of the present invention and examples thereof are disclosed in detail in the above-referenced, commonly assigned, '133 patent. Similarly, the insertion of the cathode pins 130, 135 through the wire guides 140, 141 and the seating of the electrode stack assembly 225 coupled thereto into the interior case chamber of case 90 form no part of the present invention and examples thereof are disclosed in detail in the above-referenced, commonly assigned, '133 patent.

Then, the cover 110 is placed upon the upper edge 92 of the case side wall, the upper edge 92 is crimped over the cover edge, and the joint therebetween is laser welded all in a manner that forms no part of the present invention. A connector assembly is also coupled with the exposed, outwardly extending pins 130 and 135. In one preferred embodiment, connector block 145 is disposed atop or otherwise connected to case 90 and/or cover 110, and has wire harness 155 attached thereto and potting adhesive disposed therein. However, the particular configuration of connector block 145 and its method of fabrication does not play a role in the practice of the present invention. Examples thereof are disclosed in detail in the above-referenced, commonly assigned, '133 patent.

In the illustrated embodiment, pre-formed plastic connector block 145 is placed on anode ferrule 95 and cathode ferrule 100 by guiding anode feedthrough pin 130 through connector block anode feedthrough hole 300, and then guiding cathode feedthrough pin 135 through connector block cathode feedthrough hole 305. Connector block 145 is next seated flush against the exterior surface of case 90. Anode feedthrough pin 130 is then inserted into anode crimp tube 150*b* of wire harness 155. Cathode feedthrough pin 135 is then inserted into cathode crimp tube 150*a* of wire harness 155. Crimp tubes 150*a* and 150*b* are then crimped to feedthrough pins 130 and 135. The distal or basal portions of crimp tubes 150*a* and 150*b* are crimped on insulated anode lead 151 and insulated cathode lead 152, respectively. An epoxy adhesive is then injected into voids in the connector block 145 to insulate the crimped connections, seal the wire guides 140 and 141, case 90 and ferrules 95 and 100, and provide strain relief to feedthrough pins 130 and 135 and to the feedthrough wire crimp connections. Insulated leads 151 and 152 are likewise connected to terminal connector 153 that forms the female end of a slide contact and is adapted to be connected to electronics module 360 in FIG. 3(*d*).

The life of capacitor 265 may be appreciably shortened if solvent vapor or electrolyte fluid escapes from the interior of capacitor 265. Moreover, if capacitor 265 leaks electrolyte, the electrolyte may attack the circuits to which capacitor 265 is connected, or may even provide a conductive pathway between portions of that circuit. The present invention provides a beneficial means for preventing the escape of solvent and solvent vapor from capacitor 265. More particularly, capacitor 265 most preferably includes hermetic laser welded seams between joint case 90 and cover 110, and between ferrules 95, 100, and 105 and case 90. Additionally, anode feedthrough portion 236 and cathode feedthrough portion 240 most preferably have an adhesive seal disposed therein for sealing the ferrule walls and the feedthrough wires.

The interior of capacitor 265 not occupied by the electrode stack assembly 225 is filled with electrolyte through the fill port 107 welded at fill port ferrule 105 into hole 139, aging cycles are conducted, and the fill port is then closed. The filling and aging are accomplished in a plurality of vacuum impregnation cycles and aging cycles form no part of the present invention and examples thereof are disclosed in detail in the above-referenced, commonly assigned, '133 patent. The electrolyte may be any suitable liquid electrolyte for high voltage electrolytic capacitors. In a preferred embodiment of the present invention, the electrolyte is an ethylene glycol based electrolyte having an adipic acid solute. It is contemplated that other liquid electrolytes suitable for use in high voltage capacitors may also be employed.

During capacitor charging, the ethylene glycol based electrolyte releases hydrogen gas which accumulates within the interior capacitor chamber and eventually can cause the base and cover to bulge outward. In accordance with a preferred embodiment of the present invention, hydrogen gas is released through the lumen of fill port 107 while loss of liquid or vaporized electrolyte is prevented.

It will be understood that the capacitor 265 may alternatively be formed as a case negative capacitor where case 90 and cover 110 are electrically connected to the cathode layers and are therefore at the same electrical potential as the cathode layers, i.e., at negative potential.

The preceding specific embodiments are illustrative of a capacitor structure and method of fabrication thereof and its incorporation into an IMD in accordance with the present invention. It is to be understood, therefore, that other expedients known to those skilled in the art or disclosed herein, and existing prior to the filing date of this application or coming into existence at a later time may be employed without departing from the invention or the scope of the appended claims. In the claims, means-plus-function clauses are intended to cover the structures described herein as performing the recited function and not only structural equivalents but also equivalent structures.

All patents and printed publications disclosed herein are hereby incorporated by reference herein into the specification hereof, each in its respective entirety.

We claim:

1. A layered aluminum electrolytic capacitor comprising:
    an anode layer having opposed major anode layer surfaces and an anode layer edge around the periphery of said opposed major surfaces, said anode layer formed of at least one thin metallic anode sheet etched to form certain pores extending part way through the anode sheet and certain through-etched tunnels extending all the way through the anode sheet thereby forming an etched anode sheet providing enhanced surface area, said etched anode sheet having first and second opposed major anode sheet surfaces bounded by an anode sheet edge and an anode sheet thickness, said anode sheet having a plurality of through-holes bored to extend between said first and second opposed major surfaces and through said anode sheet thickness of said etched anode sheet and an oxide layer overlying the exposed surfaces of the pores and through-holes;
    a cathode layer;
    a separator layer positioned between said anode layer and said cathode layer; and
    an electrolyte.

2. The capacitor of claim 1, wherein a plurality of anode layers, cathode layers and separator layers are stacked together to form an electrode stack assembly with said anode layers electrically coupled together and said cathode layers electrically coupled together.

3. The capacitor of claim 2, and further including:

a capacitor case having a case interior chamber for enclosing said electrode stack assembly and said electrolyte;

an anode electrical contact extending from said coupled anode layers to an anode connection terminal outside said housing; and a cathode electrical contact extending from said coupled cathode layers to outside said housing.

4. The capacitor of claim 2, wherein said anode layer is formed of a plurality of said anode sheets that are stacked so that first and second major anode sheet surfaces of adjacent stacked anode sheets are in at least partial contact.

5. The capacitor of claim 1, wherein said plurality of through-holes are spaced apart from one another by a relatively uniform distance.

6. The capacitor of claim 1, wherein said metallic anode sheet comprises aluminum foil.

7. The capacitor of claim 1, wherein said plurality of through-holes are formed by one of the group selected from punching, mechanically drilling, and laser boring.

8. The capacitor of claim 1, wherein said through-holes are sized in cross-section and length and distributed in density so as to minimize equivalent series resistance and maximize capacitance.

9. A layered aluminum electrolytic capacitor comprising:

an anode layer having opposed major anode layer surfaces and an anode layer edge around the periphery of said opposed major surfaces, said anode layer formed of at least first, second, and third anode sheets sheet etched to form certain pores extending part way through the anode sheet and certain through-etched tunnels extending all the way through the anode sheet thereby providing enhanced surface area, each said first, second and third etched anode sheet having first and second opposed major anode sheet surfaces bounded by an anode sheet edge and an anode sheet thickness, said first and second etched anode sheets having a plurality of through-holes bored to extend through said anode sheet thickness between said first and second opposed major surfaces of said first and second etched anode sheets, said third etched anode sheet disposed between said first and second etched anode sheets;

an oxide layer overlying the exposed surfaces of the pores of the first second and third etched anode sheets and the through-holes of the first and second anode sheets;

a cathode layer;

a separator layer positioned between said anode layer and said cathode layer; and an electrolyte.

10. The capacitor of claim 9, wherein a plurality of anode layers, cathode layers and separator layers are stacked together to form an electrode stack assembly with said anode layers electrically coupled together and said cathode layers electrically coupled together.

11. The capacitor of claim 10, and further including:

a capacitor case having a case interior chamber for enclosing said electrode stack assembly and said electrolyte;

an anode electrical contact extending from said coupled anode layers to an anode connection terminal outside said housing; and a cathode electrical contact extending from said coupled cathode layers to outside said housing.

12. The capacitor of claim 9, wherein said plurality of through-holes are spaced apart from one another by a relatively uniform distance.

13. The capacitor of claim 9, wherein said metallic anode sheet comprises aluminum foil.

14. The capacitor of claim 9, wherein said plurality of through-holes are formed by one of the group selected from punching, mechanically drilling, and laser boring.

15. The capacitor of claim 9, wherein said through-holes are sized in cross-section and length and distributed in density so as to minimize equivalent series resistance and maximize capacitance.

* * * * *